US012788376B2

(12) United States Patent
Mojica et al.

(10) Patent No.: US 12,788,376 B2
(45) Date of Patent: Nov. 10, 2026

(54) APPARATUSES AND METHODS FOR SEGREGATING TISSUE SAMPLES FOR MULTIPLE DIAGNOSTIC MODALITIES

(71) Applicant: Virchow Medical, Inc., San Diego, CA (US)

(72) Inventors: Wilfrido Mojica, Amherst, NY (US); Alexander Arrow, Lakeside, CA (US)

(73) Assignee: Virchow Medical, Inc.

( * ) Notice: Subject to any disclaimer, the term of this patent is extended or adjusted under 35 U.S.C. 154(b) by 463 days.

(21) Appl. No.: 18/514,870

(22) Filed: Nov. 20, 2023

(65) Prior Publication Data

US 2025/0160802 A1 May 22, 2025

(51) Int. Cl.
*A61B 10/00* (2006.01)
*A61B 10/02* (2006.01)
*B01L 3/00* (2006.01)

(52) U.S. Cl.
CPC .......... *A61B 10/0096* (2013.01); *A61B 10/02* (2013.01); *B01L 3/502* (2013.01); *B01L 3/5635* (2013.01); *A61B 2010/0225* (2013.01)

(58) Field of Classification Search
None
See application file for complete search history.

(56) References Cited

U.S. PATENT DOCUMENTS 5,663,051 A 9/1997 Van Vlasselaer et al.
5,833,860 A * 11/1998 Kopaciewicz ..... B01J 20/28033 210/473
2003/0086830 A1 5/2003 Haywood et al.
2004/0005246 A1 1/2004 Efthimiadis et al.
2006/0037903 A1* 2/2006 Smith ...................... G01N 1/40 210/240
2011/0146418 A1* 6/2011 Brevnov .............. G01N 1/4005 73/863.23
2012/0053484 A1 3/2012 Parks
2012/0061392 A1 3/2012 Beach et al.
2012/0220044 A1 8/2012 Sharma et al.
2013/0095473 A1 4/2013 Groelz
2013/0295673 A1 11/2013 Taghizadeh et al.
2013/0345596 A1 12/2013 Zimmon
2015/0056614 A1 2/2015 Mikolajczyk et al.
(Continued)

OTHER PUBLICATIONS

Mojica et. al., Front-end genomics: using an alternative approach for the recovery of high-quality DNA from core needle biopsies, 70 J. Clinical Pathology 488 (Oct. 24, 2016).
(Continued)

*Primary Examiner* — P. Kathryn Wright
(74) *Attorney, Agent, or Firm* — Spencer Fane, LLP

(57) ABSTRACT

Apparatuses and methods for recovering solid tissue and dislodged cells ("D-cells") from a biopsy are disclosed herein. In an embodiment, a biopsy container apparatus includes a sample collection container, a basket sieve, and a buffer container. The sample collection container includes a reagent chamber. The basket sieve is configured for removable attachment at least partially within the sample collection container and includes a sieve surface configured to pass the D-cells from the biopsy but not the solid tissue from the biopsy. The buffer container is configured for removable attachment to the sample collection container and includes a buffer chamber.

19 Claims, 11 Drawing Sheets

(56) References Cited

U.S. PATENT DOCUMENTS

| | | | | |
|---|---|---|---|---|
| 2015/0289856 | A1* | 10/2015 | Saqi | A61B 10/0096 422/534 |
| 2018/0361386 | A1* | 12/2018 | Hjelseth | B01L 3/561 |
| 2019/0185799 | A1* | 6/2019 | Katou | C12M 23/24 |
| 2019/0242798 | A1* | 8/2019 | Gellibolian | C12N 15/1017 |
| 2021/0079328 | A1 | 3/2021 | Barousse et al. | |
| 2024/0117406 | A1* | 4/2024 | Kawabe | B01L 3/5021 |
| 2024/0252155 | A1 | 8/2024 | Saqi et al. | |

OTHER PUBLICATIONS

Mojica et al., Core needle biopsy wash as a tool for acquiring additional diagnostic material for laboratory testing, J. Clinical Pathology (Online) (Mar. 1, 2021), https://jcp.bmj.com/content/75/5/345.

Padmanabhan et al., Improving Adequacy of Small Biopsy and Fine-Needle Aspiration Specimens for Molecular Testing by Next-Generation Sequencing in Patients with Lung Cancer, 141 Arch Pathol Lab Med 402 (Mar. 1, 2017).

Arshad et al., Cellular Material from Core Needle Biopsy Washes are Molecularly Representative of the Corresponding Parent Tissue that is Formalin Fixed and Paraffin Embedded (Poster) 111th Annual USCAP (Mar. 19, 2022).

International Search Report and Written Opinion issued Jan. 13, 2025 in corresponding International Application No. PCT/US2024/046776.

International Search Report corresponding to PCT/US2025/055918 dated Mar. 25, 2026.

* cited by examiner

APPARATUSES AND METHODS FOR SEGREGATING TISSUE SAMPLES FOR MULTIPLE DIAGNOSTIC MODALITIES

BACKGROUND

Technical Field

The present disclosure generally relates to apparatuses and methods for segregating tissue samples for multiple diagnostic modalities. More specifically, the present disclosure relates to biopsy container apparatuses for recovering solid tissue and dislodged cells from a biopsy and their corresponding methods of use.

Related Application

The systems and methods of the present disclosure can be used in combination with the apparatuses and methods of U.S. patent application Ser. No. 18/468,416, filed Sep. 15, 2023, entitled "Methods and Systems for Recovering Assessable Analytes from Core Needle Biopsies," the entire contents of which is incorporated herein by reference.

BACKGROUND INFORMATION

Solid tumor diagnostic procedures typically involve a tissue biopsy. Traditionally, a biopsy involves a substantial amount of tissue being surgically excised from a tumor or suspected affected tissue in a patient. The tissue, once removed from the patient's body, is processed and subsequently can be used for a number of different types of diagnostic tests.

In recent years, biopsy tools and techniques have advanced to be less invasive, with dramatically smaller tissue samples. Surgically-excised biopsies have largely been replaced by core needle biopsy (CNB) tools. Smaller biopsies are less traumatic for patients, quicker for the clinician to perform, and less expensive for the healthcare system in general. Hence, standard biopsy tissue size has declined significantly between the period before approximately 2010 and the years thereafter. The disadvantage of smaller biopsies is that they provide less tissue for pathologists to examine and analyze to render diagnostic opinions.

At the same time, diagnostic testing modalities have expanded to include an increased number of tests aimed at identifying molecular changes. The declining tissue biopsy size and the expanding quantity of testing required of the biopsied tissue has created an imbalance between tissue supply and demand. The result is that in some cases, clinicians make treatment decisions for patients with less diagnostic information than they would like. In other cases, patients are subjected to a second biopsy. The risk that a biopsy sample will have insufficient tissue to allow for the clinically-indicated tests to be performed is a big enough problem that it has several unofficial names, with "Tissue Exhaustion" being the most common. Tissue Exhaustion rates for core needle biopsies are reported in literature to be between 22-82% of all biopsies.

An imbalance therefore exists between the typical amount of tissue yielded from a CNB and the typical amount of tissue needed for testing. Healthcare quality is impacted by the shortfall in the quality and quantity of substrate available for molecular testing. This ultimately affects patient care, with many specimens received in the pathology laboratory not being available for molecular testing, resulting in these patients missing out on the improved treatment options associated with precision medicine (defined as using molecular testing to find a mutation to guide therapy).

It is unfortunate that standard tissue biopsy handling practices today result in some of the harvested cells being discarded along with medical waste. These cells come from the patient, unavoidably dislodged (referred to hereafter as D-cells) from the tissue due to the trauma associated with of the sharp edge of the CNB needle cutting through tissue and then pulling back into the metal CNB tube (e.g., as shown in FIGS. 7 and 8). These cells are not visible to the human eye. They contain valuable genetic information, but they are simply not noticed by the clinician or technician holding the CNB tube and placing the tissue into a standard cup-like container after harvesting. The current standard of care involves fixation of the tissue with formalin, in a process called formalin-fixation, paraffin embedding (FFPE), and which is known to create sub-optimal results with molecular testing.

SUMMARY

The present disclosure provides a biopsy container apparatus that allows a clinician who performs a core needle biopsy to deposit the harvested tissue in such a way that it recovers cells that are dislodged ("D-cells") from the solid tissue that is procured during the biopsy procedure. D-Cells are an unrealized resource for diagnostic testing, mainly because cells are below the acuity of the human eye. This valuable biologic resource is typically discarded, but the apparatuses s and methods of the present disclosure enable its recovery for diagnostic testing.

As discussed in more detail below, the biopsy container apparatus disclosed herein enables a clinician who performs a core needle biopsy to deposit the tissue in such a way that it contains and preserves the microscopic accompanying portions (D-cells) of the biopsied tissue that would otherwise be inadvertently discarded. More specially, the biopsy container apparatus disclosed herein enables cells that are dislodged from tissue that is procured during a biopsy procedure to be kept and segregated from the tissue that will be sent for standard pathology laboratory processing, using a specialized removable sieve suspended within a multi-functional watertight container. These recovered cells (D-cells) constitute an unrealized resource for diagnostic testing. This resource is typically discarded, but the apparatuses and methods of the present disclosure ensure recovery for diagnostic testing.

A first aspect of the present disclosure is to provide a biopsy container apparatus for recovering solid tissue and D-cells from a biopsy. The biopsy container apparatus includes a sample collection container, a basket sieve, and a buffer container. The sample collection container includes a reagent chamber. The basket sieve is configured for removable attachment at least partially within the sample collection container and includes a sieve surface configured to pass the D-cells from the biopsy but not the solid tissue from the biopsy. The buffer container is configured for removable attachment to the sample collection container and includes a buffer chamber.

A second aspect of the present disclosure is to provide another biopsy container apparatus for recovering solid tissue and D-cells from a biopsy. The biopsy container apparatus includes a sample collection container, a basket sieve, and a buffer container. The sample collection container includes a reagent. The basket sieve is configured for removable attachment at least partially within the sample collection container and includes a sieve surface configured to pass the D-cells from the biopsy but not the solid tissue from the biopsy. The buffer container is configured for removable attachment to the sample collection container and includes a buffer.

A third aspect of the present disclosure is to provide another biopsy container apparatus for recovering solid tissue and D-cells from a biopsy. The biopsy container apparatus includes an upper chamber, a lower chamber, a sieve surface and a solid surface. The sieve surface is located between the upper chamber and the lower chamber and is configured to pass the D-cells from the biopsy but not the solid tissue from the biopsy. The solid surface is movably attached with respect to the sieve surface and configured to translate between (i) a first configuration in which the solid surface overlaps the sieve surface to prevent the D-cells from passing through the sieve surface and (ii) a second configuration in which the solid surface is moved away from the sieve surface to permit the D-cells to pass though the sieve surface from the upper chamber to the lower chamber.

A fourth aspect of the present disclosure is to provide a method of recovering solid tissue and D-cells from a biopsy using a buffer container apparatus including a buffer container, a basket sieve and a sample collection container. The method includes depositing the solid tissue and the D-cells from the biopsy into a buffer solution within the buffer container, removing the buffer container from the basket sieve and the sample collection container, pouring the solid tissue, the D-cells and the buffer solution into the basket sieve while the basket sieve is located within the sample collection container, removing the basket sieve with the solid tissue from the sample collection container, placing the basket sieve with the solid tissue into a sealed container for tissue processing, and sealing a mixture including the D-cells, the buffer solution and the reagent for diagnostic testing.

Other objects, features, aspects and advantages of the apparatuses and methods disclosed herein will become apparent to those skilled in the art from the following detailed description, which, taken in conjunction with the annexed drawings, discloses exemplary embodiments of the disclosed apparatuses and methods.

BRIEF DESCRIPTION OF THE DRAWINGS

Referring now to the attached drawings which form a part of this original disclosure.

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

Figure 1:
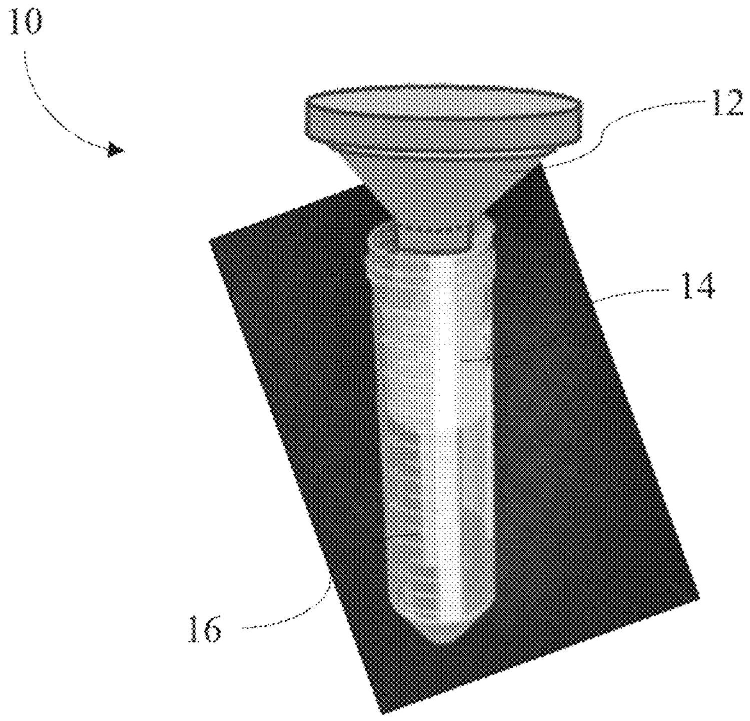
FIG. 1 illustrates a perspective view of a first example embodiment of a biopsy container apparatus in accordance with the present disclosure.
Figure 2:
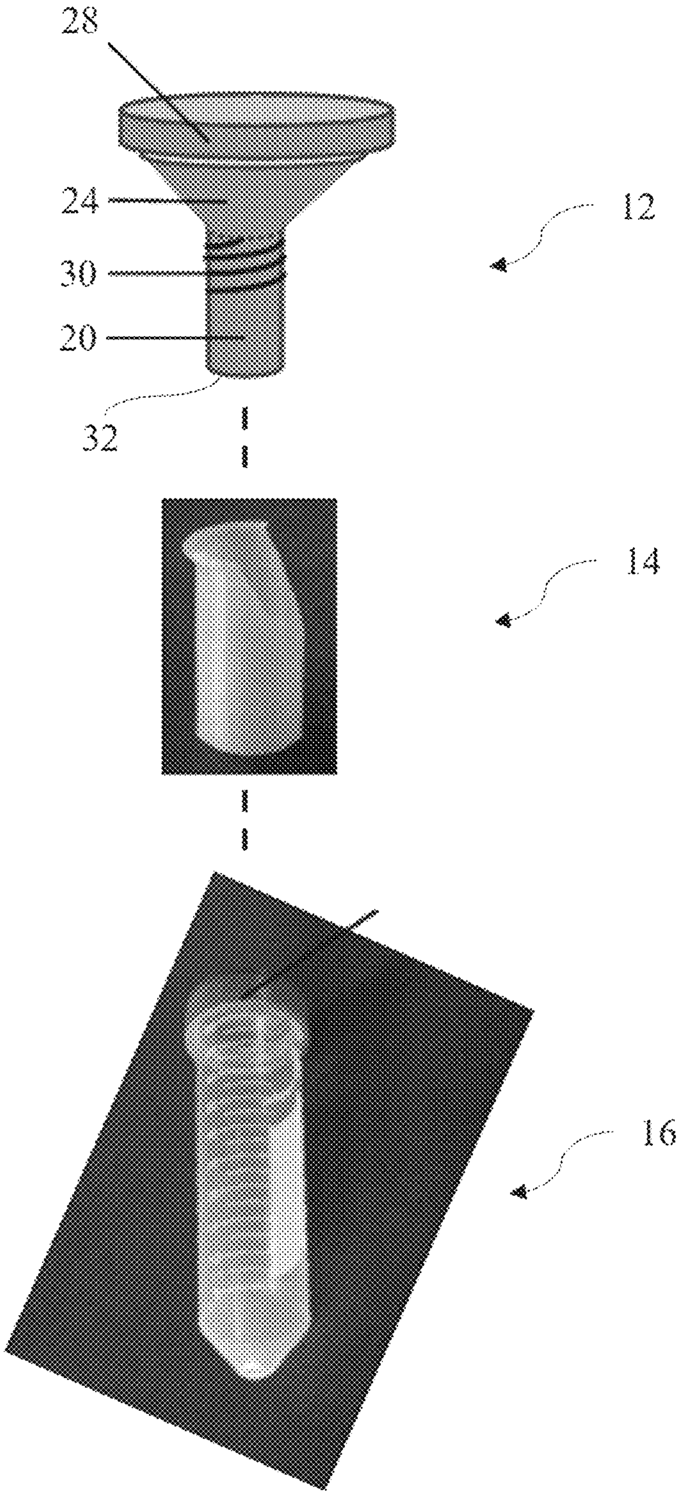
FIG. 2 illustrates an exploded view of the biopsy container apparatus of FIG. 1.
Figure 3:
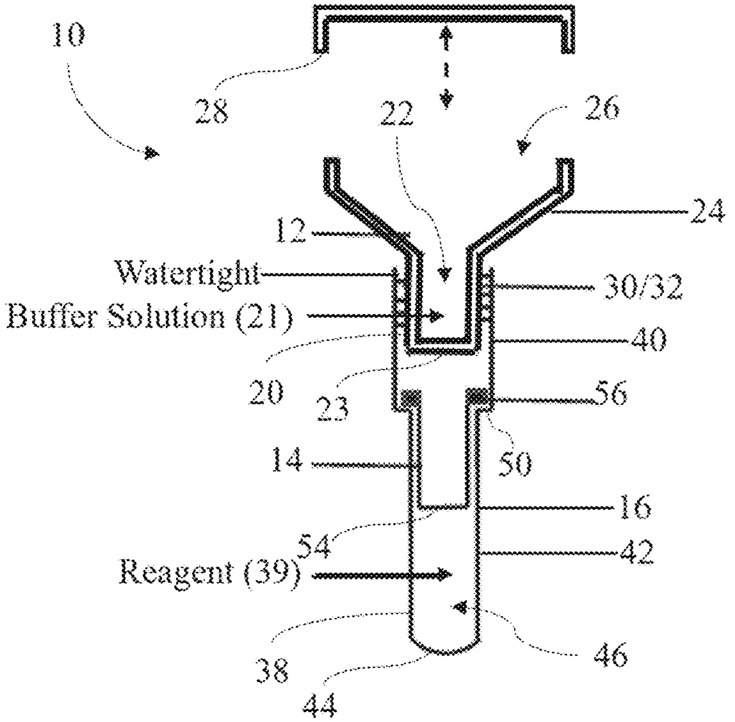
FIG. 3 illustrates a cross-sectional view of the biopsy container apparatus of FIG. 1.

FIGS. 1 to 3 illustrate an example embodiment of a biopsy container apparatus 10 for recovering solid tissue and D-cells from a biopsy in accordance with the present disclosure. In the illustrated embodiment, the biopsy container apparatus 10 includes a buffer container 12, a basket sieve 14 and a sample collection container 16, which are three separable elements that can be attached prior to a biopsy and then separated during the method of use disclosed herein. As illustrated, the buffer container 12 and basket sieve 14 are configured for removable attachment to the sample collection container 16. FIG. 1 illustrates the buffer container 12, the basket sieve 14 and the sample collection container 16 attached together, while FIG. 2 shows the buffer container 12, the basket sieve 14 and the sample collection container 16 detached from each other.

The buffer container 12 includes a buffer chamber 20 for storing or receiving buffer solution 21. The bottom edge 23 of the buffer chamber 20 is sealed and watertight so that the inner space 22 of buffer chamber 20 retains the buffer solution 21. In an embodiment, the buffer chamber 20 is pre-filled with the buffer solution 21 within the inner space 22. In an embodiment, the buffer solution 21 is a sterile phosphate-buffered saline (PBS) buffer solution. In an embodiment, the buffer chamber 20 includes between 1 and 2 mL of buffer solution. In an embodiment, the buffer chamber 20 is pre-filled with approximately 1-2 ml of buffer solution. While PBS is the most likely choice of buffer, any similar buffer solution, such as Buffer Roswell Park Memorial Institute ("RPMI 1640 Media") Buffer Solution, would serve the same purpose.

In the illustrated embodiment, the buffer container 12 has a funnel shape to assist a user in depositing a biopsy sample from a core needle into the buffer solution 21 within the buffer chamber 20. More specifically, the buffer container 12 includes a funnel portion 24. The funnel portion 24 flares outwardly from bottom to top, while the buffer chamber 20 has a generally cylindrical shape for insertion into the basket sieve 14 and/or the sample collection container 16 as shown in FIG. 3. The funnel portion 24 is configured to guide the solid tissue and the D-cells from the biopsy into the buffer chamber 20 when ejected from a core needle, as discussed in more detail below.

In the illustrated embodiment, the buffer container 12 includes a top opening 26 and a lid 28. The lid 28 attaches to the top of the funnel portion 24 to cover the top opening 26 and enclose the inner space 22 so that the buffer solution 21 does not spill if the biopsy container apparatus 10 is inverted. The lid 28 can be attached by being screwed onto the top of the funnel portion 24, or by another suitable attachment mechanism. In an embodiment, the lid 28 is configured to attach to both the buffer container 12 and the sample collection container 16, so that a user can remove the lid 28 form the buffer container 12 when beginning use of the biopsy collection apparatus 10 and then later place the lid 28 on the sample collection container 16 to seal its contents, as discussed in more detail below.

Figure 5:
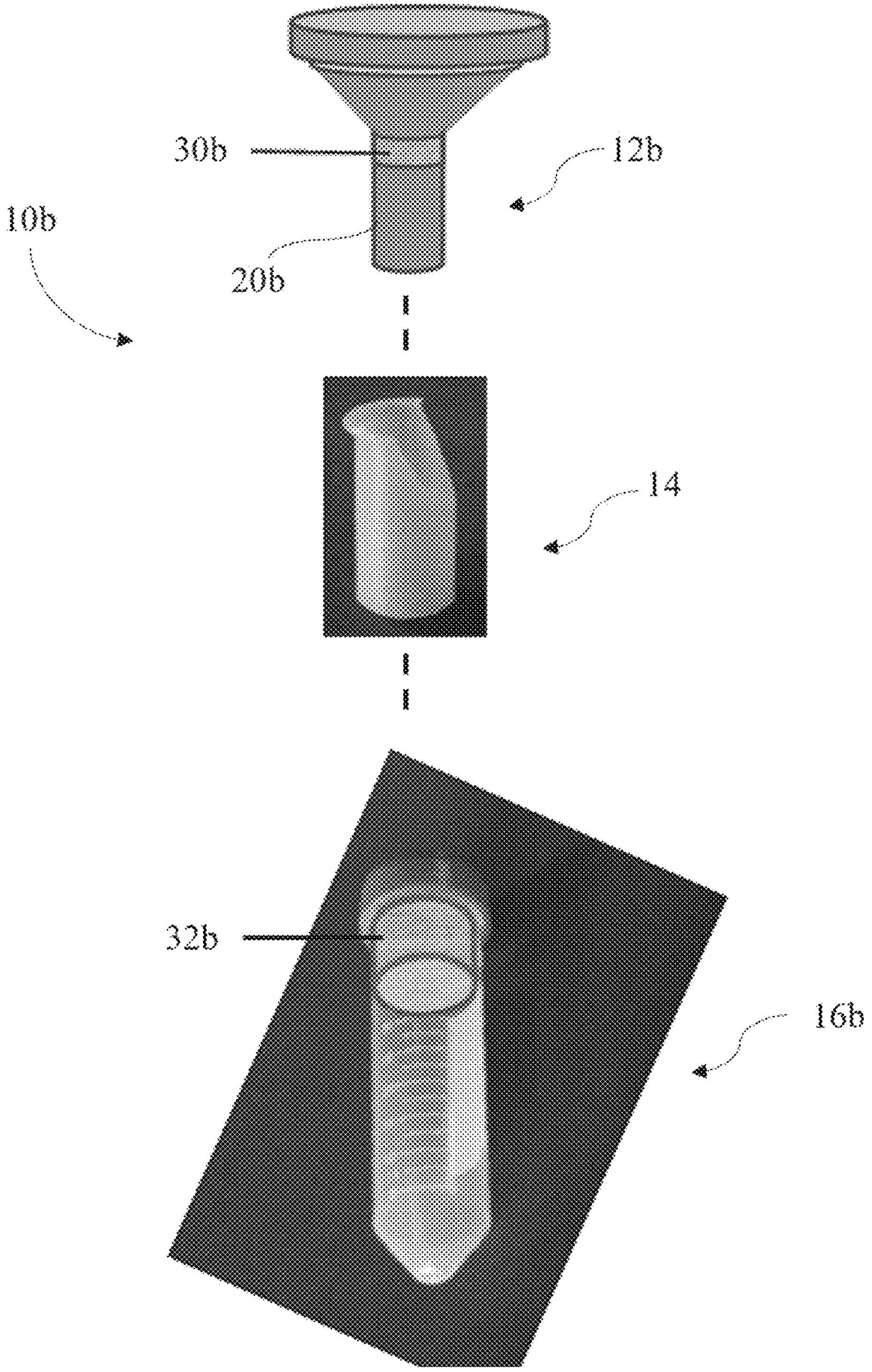
FIG. 5 illustrates an exploded view of a third example embodiment of a biopsy container apparatus in accordance with the present disclosure.

In the illustrated embodiment, the buffer container 12 also includes a first attachment mechanism 30 to enable attachment to a second attachment mechanism 32 of the sample collection container 16. More specifically, the outer surface of the buffer chamber 20 includes the first attachment mechanism 30. In the illustrated embodiment, the second attachment mechanism 32 is located on the inner surface of the sample collection container 16. The first attachment mechanism 30 and the second attachment mechanism 32 enable removable attachment of the buffer container 12 to the sample collection container 16, with the buffer container 12 located at least partially within the sample collection container 16. As shown in FIG. 3, the first attachment mechanism 30 and the second attachment mechanism 32 create a watertight seal between the outer surface of the buffer container 12 and the inner surface of the sample collection 16 container so that liquid will not spill from the sample collection container 16 if the biopsy container apparatus 10 is inverted. In the embodiment illustrated in FIGS. 1 to 3, the first attachment mechanism 30 and the second attachment mechanism 32 are corresponding screw threads that enable the buffer container 12 to screw into the sample collection container 16. In an alternative example embodiment of a biopsy container apparatus **10*b* illustrated in FIG. 5, the first attachment mechanism 30*b* includes a rubber sleeve on the outer surface of the buffer chamber 20*b* of the buffer container 12*b*, and the second attachment mechanism 32*b* includes a rubber sleeve on the inner surface of the sample collection container 16*b***.

The sample collection container 16 includes a reagent chamber 38 for storing or receiving a reagent 39. In FIG. 3, the sample collection container 16 includes an upper portion 40 and a lower portion 42, with the reagent chamber 38 located within and/or formed by the lower portion 42. The bottom edge 44 of the sample collection container 16 is sealed and watertight so that the reagent chamber 38 retains the reagent 39. In the illustrated embodiment, the reagent chamber 38 is pre-filled with the reagent 39 within the inner space 46. In an embodiment, the reagent 39 is a solution for lysing cells and preserving nucleic acids that is approximately 2× the normal concentration of an off-the-shelf cell lysing reagent. In an embodiment, the reagent 39 is Zymo DNA/RNA Shield™ reagent, or an equivalent for lysing cells and preserving nucleic acids which is 2× the normal concentration defined by and provided by Zymo. In an embodiment, the reagent chamber 38 includes between 1 and 2 mL of reagent 39. In an embodiment, the reagent chamber 38 is pre-filled with 1-2 ml of double-concentration cell lysis/nucleic acid stabilization reagent 39. In an embodiment, the reagent chamber 38 includes a first amount of reagent 39, and the buffer chamber 20 includes a second amount of buffer solution 21 that is approximately equal in volume to the first amount of reagent.

In the illustrated embodiment, both the upper portion 40 and the lower portion 42 of the sample collection container are generally cylindrical, with the lower portion 42 having a smaller inner diameter than the upper portion 40, as shown in FIG. 3. As also shown in FIG. 3, the sample collection container 16 can include an internal ledge 50 between the upper portion 40 and the lower portion 42 which is configured to support the basket sieve 14. In an alternative embodiment, the upper portion 40 and the lower portion 42 can be approximately the same diameter, and the sample collection container 16 can include an internal ridge line between the upper portion 40 and the lower portion 42 which is configured to support the basket sieve 14.

Figure 4:
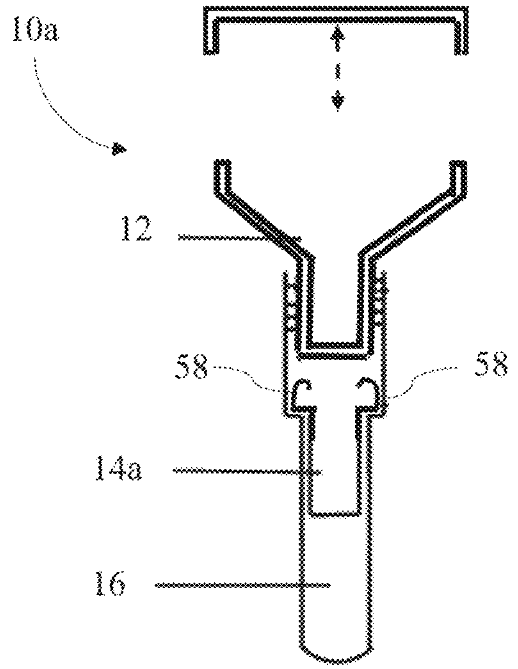
FIG. 4 illustrates a cross-sectional view of a second example embodiment of a biopsy container apparatus in accordance with the present disclosure.

The basket sieve 14 includes a sieve surface 54 configured to pass the D-cells from a biopsy but not solid tissue from the biopsy. The pore size of the sieve is approximately 40-100 microns in diameter per pore (the pore aperture size) to allow D-cells 62 to fall through. In the illustrated embodiment, the sieve surface 54 is the lower surface of the basket sieve 14. As seen in FIG. 3, the basket sieve 14 also includes a lip 56 that rests on the ledge 50 or ridge line of the sample collection container 16 so that the basket sieve 14 is suspended within the sample collection container 16 above the reagent chamber 38 and below the buffer container 12. As seen in the alternate example embodiment of a biopsy container apparatus **10*a* in FIG. 4, the basket sieve 14*a* can also include loop-like or hook-like vertical members 58 to assist a user in lifting the basket sieve 14*a* upward to remove the basket sieve 14*a* (and the tissue it carries) from the sample collection container 16** during use.

As seen in FIG. 3, when the buffer container 12, the basket sieve 14 and the sample collection container 16 are attached, the basket sieve 14 is suspended above the reagent chamber 38 of the sample collection container 16, and the buffer container 12 is suspended above the basket sieve 14 by attachment of the first attachment mechanism 30 to the second attachment mechanism 32. Those of ordinary skill in the art will recognize from this disclosure that there are other ways of attaching the elements so that they are generally arranged as shown in FIG. 3.

As also seen in FIG. 3, when the basket sieve 14 is attached to the sample collection container 16, the basket sieve 14 is located at least partially within the sample collection container 16. In FIG. 3, the basket sieve 14 is located entirely within the sample collection container 16. Similarly, the buffer container 12 can be located at least partially or fully within the sample collection container 16 when attached to the sample collection container 16. In FIG. 3, the buffer container 12 is located partially within the sample collection container 16, with the reagent chamber 20 located within the sample collection container 16 but the funnel portion 24 located outside of the sample collection container 16. More specifically, the buffer chamber 20 of the buffer container 12 is at least partly located within the sample collection container 16, and the funnel portion 24 of the buffer container 12 is at least partially located outside of the sample collection container 16. Those of ordinary skill in the art will recognize from this disclosure that there are various ways to arrange the buffer container 12, the basket sieve 14 and the sample collection container 16 without departing from the spirit and scope of the present disclosure. In other embodiments, the buffer container 12 and/or basket sieve 14 can be removably attached outside of the sample collection container 16.

Figure 6:
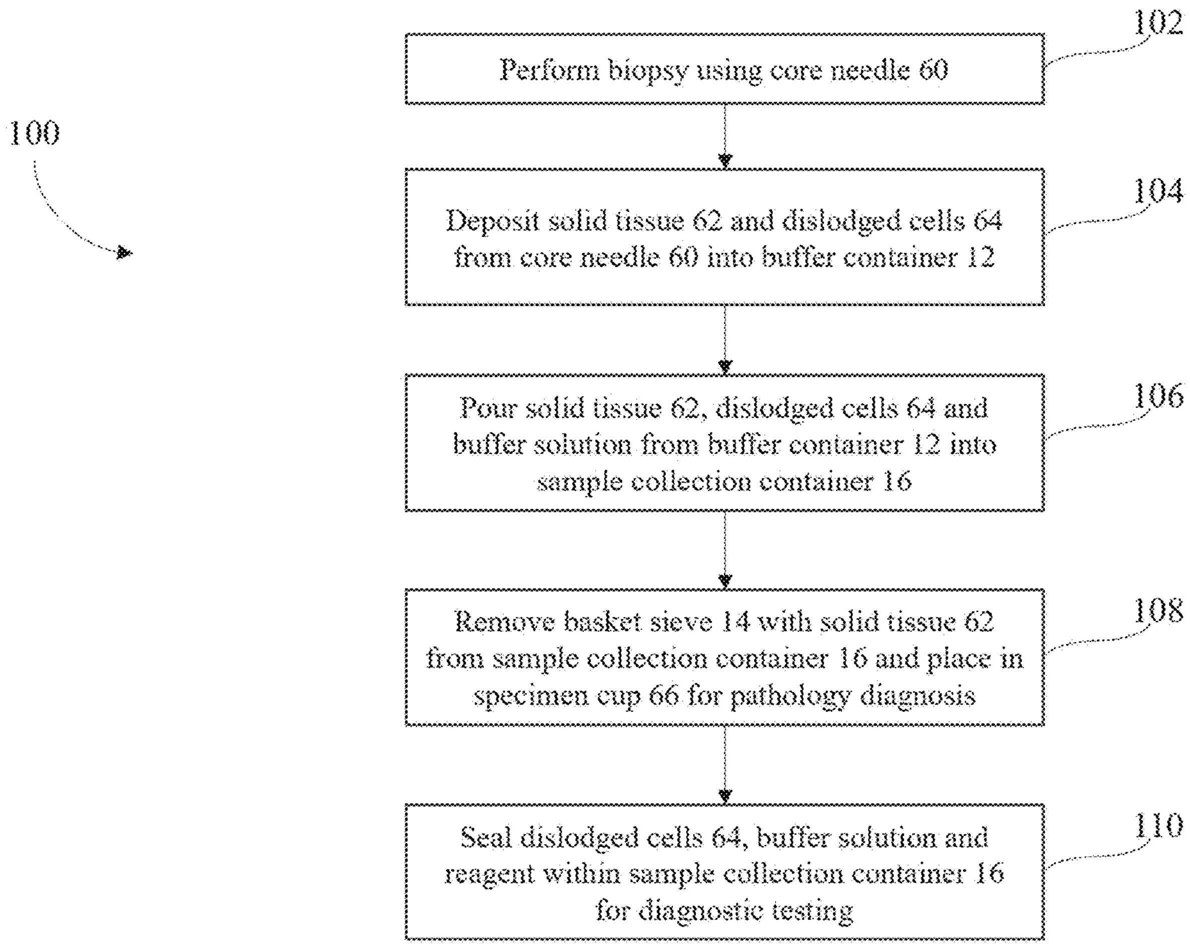
FIG. 6 illustrates an example embodiment of a method of using a biopsy container apparatus in accordance with the present disclosure.
Figure 7:
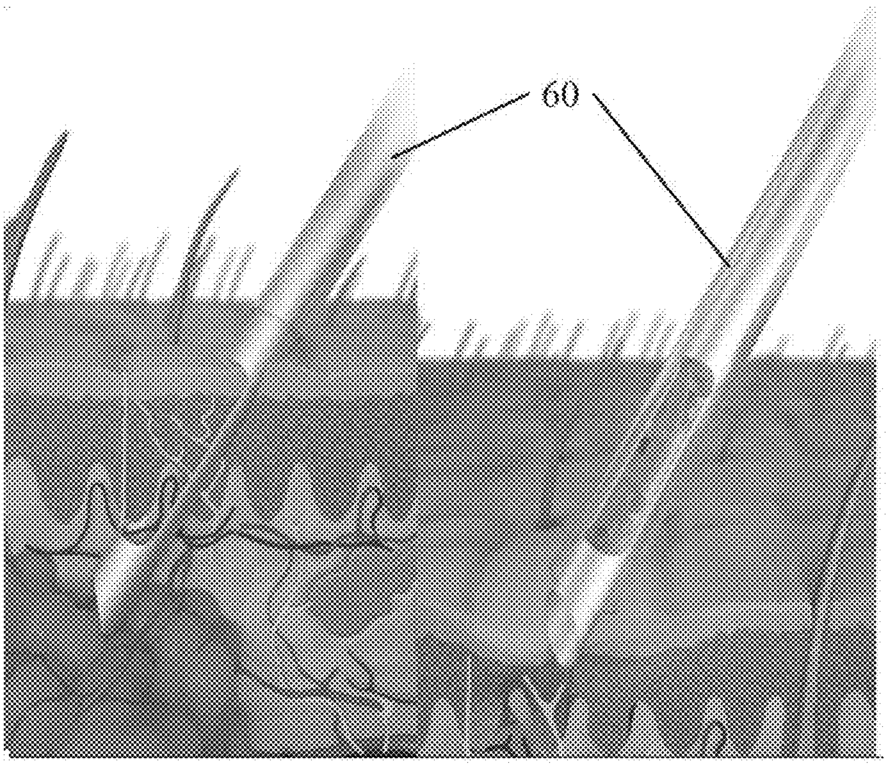
FIGS. 7 to 12 illustrate example embodiments of the steps of the method of FIG. 6.
Figure 8:
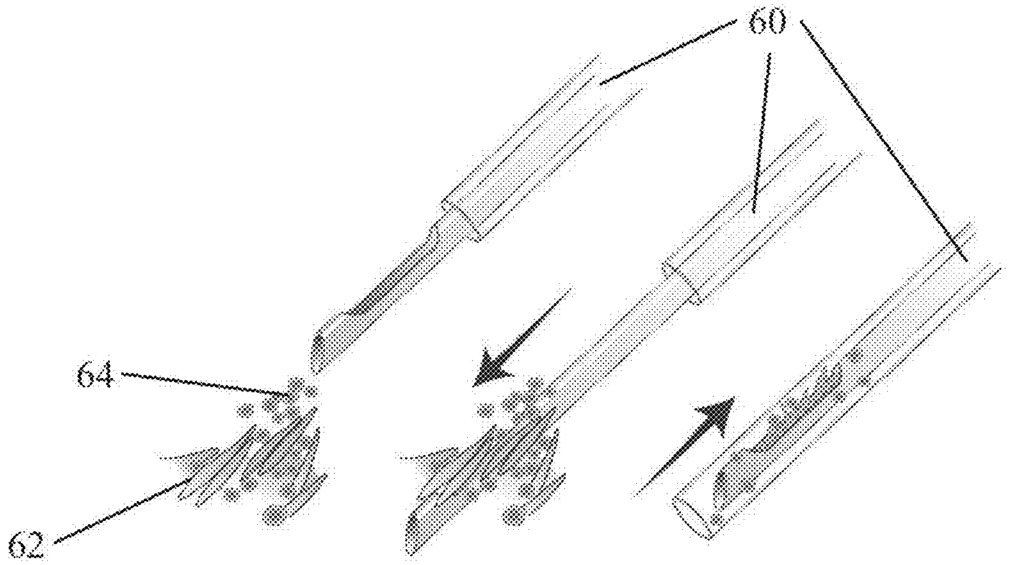
Figure 9:
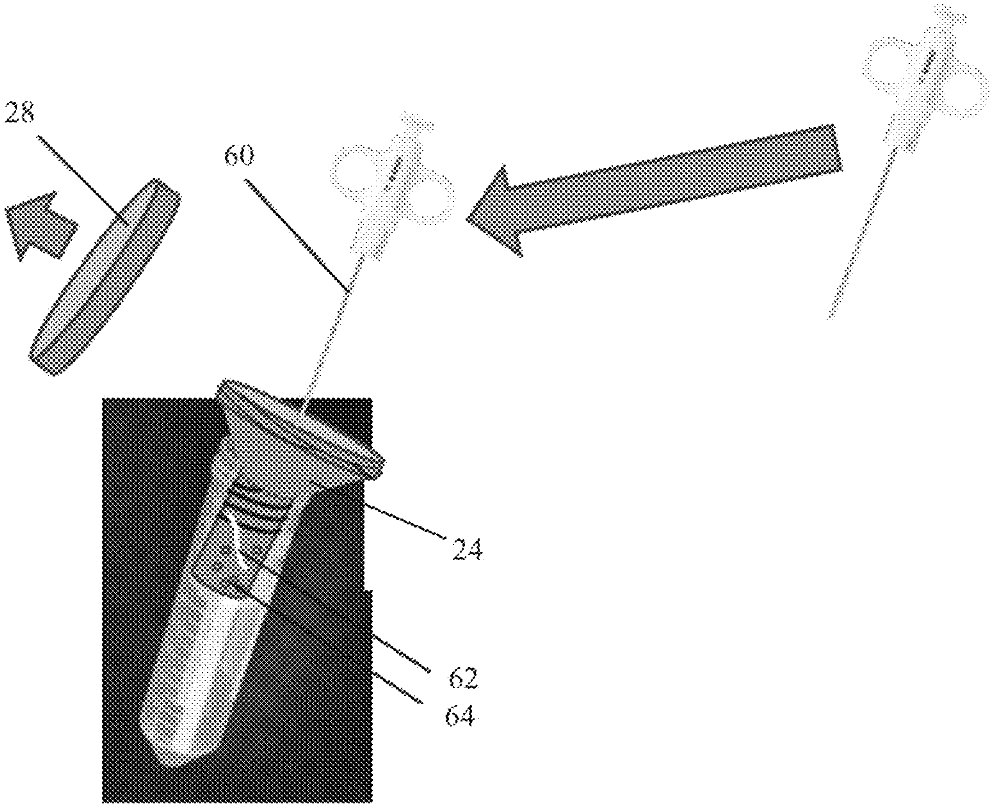
Figure 10:
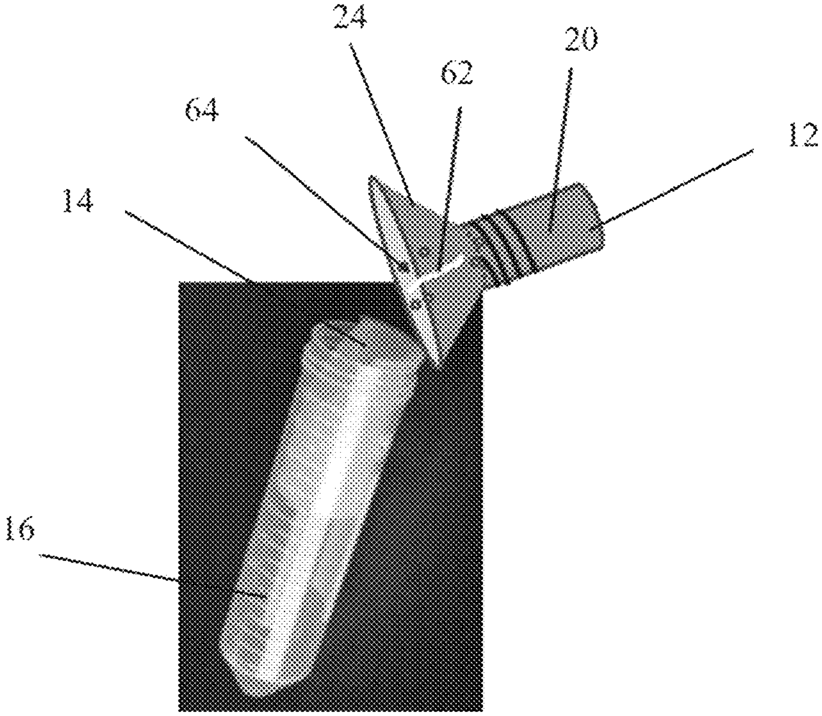

FIG. 6 shows an example embodiment of a method 100 of recovering solid tissue and D-cells from a biopsy using a biopsy container apparatus 10 in accordance with the present disclosure. FIGS. 7 to 12 illustrate various steps of the method 100. Those of ordinary skill in the art will recognize from this disclosure that certain steps can be added, removed or altered without departing from the spirit and scope of the present disclosure.

At step 102 (FIGS. 7 and 8), a user (e.g., interventional radiologist or other clinical user) uses a core needle 60 to harvest an image guided biopsy from a patient with suspicious mass lesion inside his or her body (e.g., liver, lung, kidney, etc). The core needle 60 removes both solid tissue 62 and dislodged cells 64 (D-cells) from the patient. The funnel portion 24 makes it easy for the user to spacially coordinate the CNB needle tip and the target area and provides a convenient way to for the user to place the tip of the needle (and therefore the tissue sample) into the buffer solution 21. Since the user's hand is approximately eight (8) inches away from the needle tip (holding the handle; not the tip), and the other hand is holding a buffer container or a conventional tray or rack in which the container is placed (not pictured) or otherwise unavailable and generally not used to guide the tip of the needle, maneuvering the tip of the needle into a small target is not easy. The larger funnel shape 24 of the present disclosure makes the target easier to hit.

At step 104 (FIG. 9), the user removes the lid 28 and places the tip of the core needle 60 within the funnel portion 24 of the buffer container 12. The user deposits the contents of the core needle 60 including the solid tissue 62 and the D-cells 64 into the buffer solution 21 within the buffer-containing closed end of the funnel shape 24. The user may swirl the CNB needle tip to deposit the harvested tissue sample by moving the needle in a roughly circular fashion in the closed distal end of the funnel shape 24, somewhat like the motion one would use with a manual egg beater, if the egg beater were a hollow-bore needle.

Figure 11:
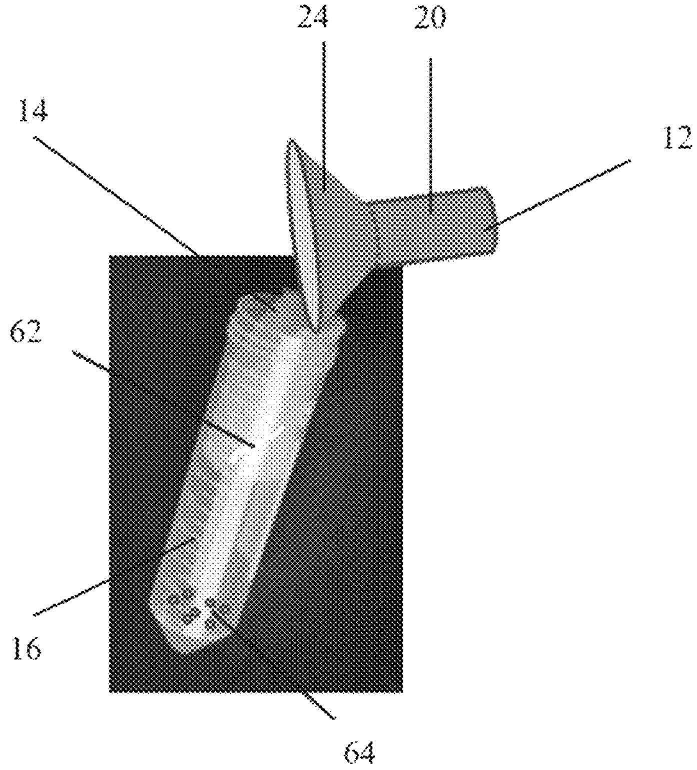
Figure 12:
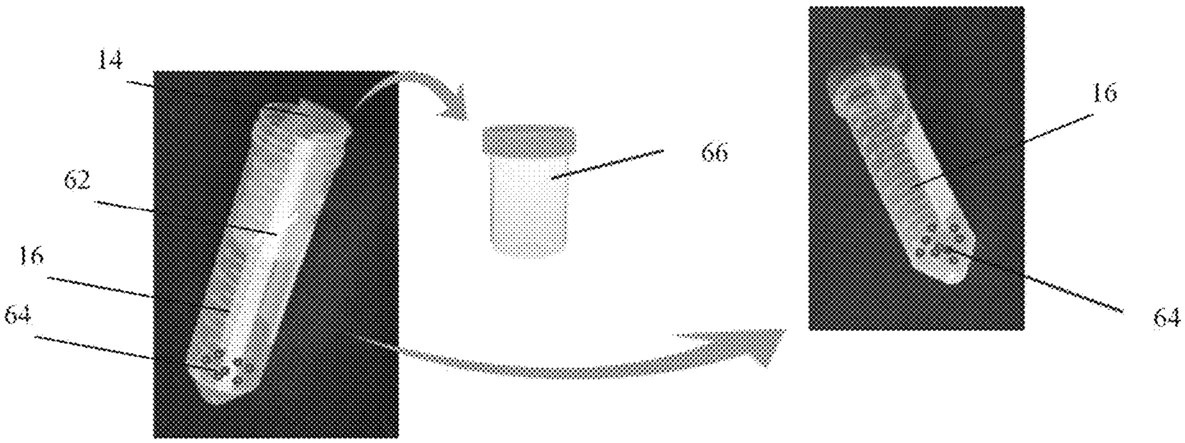

At step 106 (FIGS. 10 and 11), the user removes the buffer container 12 from the sample container 16. The user removes the buffer container 12 from the sample collection container 16, for example, by detaching the first attachment mechanism 30 and the second attachment mechanism 32. The user then pours the contents of the buffer container 12 (the solid tissue 62, the D-cells 64 and the buffer solution 21) into the basket sieve 14 that is located within the sample collection container 16. As seen in FIG. 11, the solid tissue 62 is captured by the sieve floor 54 and remains within the basket sieve 14, while the buffer solution 21 and the D-cells 64 fall through the sieve floor 54 and mix with the reagent 39 in the reagent chamber 38 of the sample collection container 16. Since the reagent 39 is 2× concentrated, the additional volume of buffer solution 21 and dislodged cells 64 restores the reagent concentration to normal.

At step 108 (FIG. 12), the user removes the basket sieve 14 containing the solid tissue 62 from the sample collection container 12. The user places the basket sieve 14 containing the solid tissue 62 into a specimen cup 66 containing formalin. The specimen cup 66 is sealed and sent to a tissue pathology lab. Thereafter the tissue core can undergo traditional tissue processing, for example, to create a glass slide image for the pathologist to make a diagnosis.

At step 110 (FIG. 12), the user seals the sample collection container 16 including the dislodged cells 64, the buffer solution 21 and the reagent 39 for diagnostic testing. For example, the user can send the sealed sample collection container 16 and its contents to a molecular lab for molecular diagnostic testing. At this point the buffer container 12 and basket sieve 14 have been removed and the sealed sample collection container 16 includes the mixed buffer solution 21, reagent 39 and D-cells 64.

Figure 13:
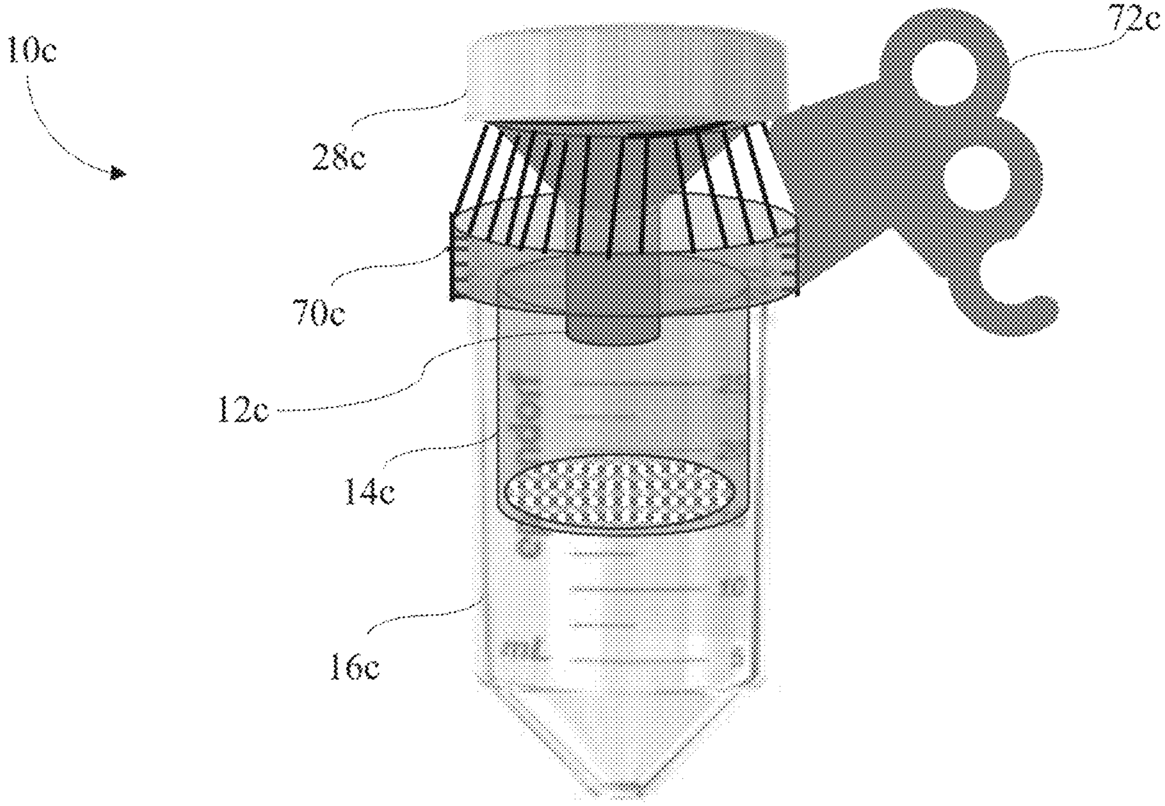
FIG. 13 illustrates a perspective view of a fourth example embodiment of a biopsy container apparatus in accordance with the present disclosure.
Figure 14:
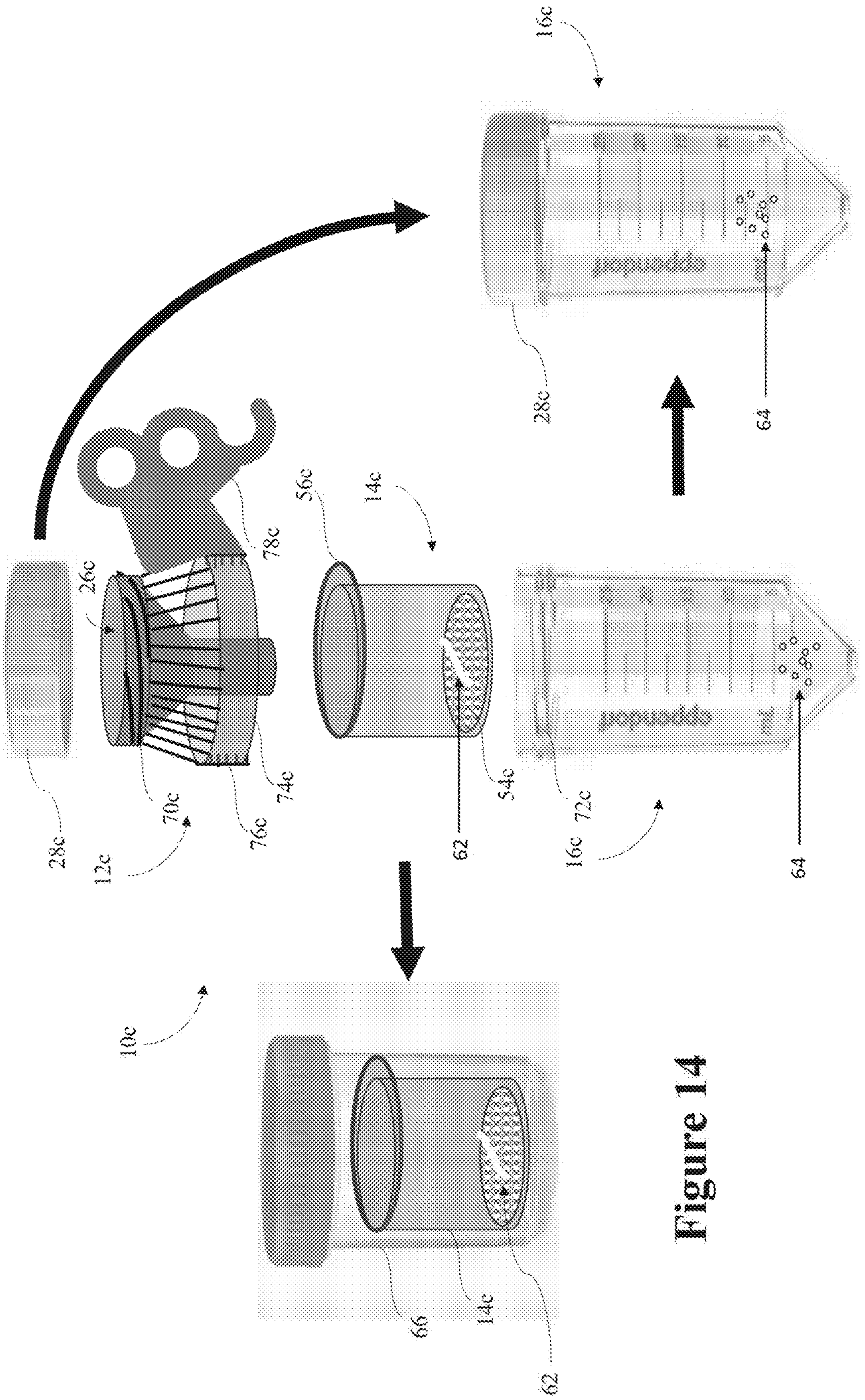
FIG. 14 illustrates an exploded view of the biopsy container apparatus of FIG. 13.

FIGS. 13 and 14 illustrate an alternative embodiment of a biopsy container apparatus 10*c* in accordance with the present disclosure. Those of ordinary skill in the art will recognize that various elements of the biopsy container apparatus 10*c* can be modified with various elements of the other embodiments of biopsy containers discussed herein, and vice versa. In FIGS. 13 and 14, the same reference numbers are used to describe the same elements as biopsy container apparatus 10.

In the illustrated embodiment, the biopsy container apparatus 10*c* includes a buffer container 12*c*, a basket sieve 14*c* and a sample collection container 16*c*. As with the biopsy container apparatus 10, the buffer container 12*c* and basket sieve 14*c* are configured for removable attachment to the sample collection container 16*c*.

In the illustrated embodiment, the buffer container 12*c* is generally similar to the buffer container 12 discussed herein. The buffer container 12*c* includes a buffer chamber 20*c*, a funnel portion 24*c*, a top opening 26*c* and a lid 28*c*. As seen in FIG. 14, the lid 28*c* is configured to fit both the buffer container 12*c* and the sample collection container 16*c*, so that a user can remove the lid 28*c* from the buffer container 12*c* when beginning to use the biopsy container apparatus 10*c*, and then later place the lid 28*c* on the sample collection container 16*c* to seal the D-cells 64 within the sample collection container 16*c*. More specifically, as seen in FIG. 14, the buffer container 12*c* includes threads 70*c* at the top of the funnel portion 24*c*, and the sample collection container 16*c* includes threads 72*c* near its top rim. The threads 70*c* and the threads 72*c* are the same size so that the lid 28*c* is configured to screw onto both the threads 72*c* of the buffer container 12*c* and the threads 72*c* of the sample collection container 16*c*.

In the illustrated embodiment, the buffer container 12*c* also includes a skirt 74*c* with threads 76*c* on its inner surface. The threads 76*c* on the inner surface on the skirt 74*c* are configured to mate with the threads 72*c* of the sample collection 16*b*. So the threads 76*c* on the inner surface on the skirt 74*c* attach to the threads 72*c* of the sample collection 16*c* when the lid 28*c* is threaded onto the threads 70*c* at the top of the funnel portion 24*c*, and the lid 28*c* is then threaded onto the threads 72*c* of the sample collection container 16*c* once the threads 76*c* on the inner surface on the skirt 74*c* are unthreaded from the threads 72*c* of the sample collection 16*c*.

In the illustrated embodiment, the buffer container 12*c* also includes a handle 78*c* protruding from skirt 74*c*. The handle 78*c* enables the user to (i) hold the biopsy container apparatus 10*c* with one hand while the other hand unscrews the lid 28*c*, (ii) hold the biopsy container apparatus 10*c* steady with one hand while the other hand operates a core needle 60 containing a tissue sample, maneuvering it into the funnel portion 24*c* and depositing its contents therein, (3) unscrew the buffer container 12*bc* from the sample collection container 16*c*, and (4) lift and pour the contents of the buffer container 12*c* (e.g., the solid tissue 62, the D-cells 64 and the buffer solution 21) into the basket sieve 14*c* and sample collection container 16*c*.

In the illustrated embodiment, the basket sieve 14*c* is generally similar to the basket sieve 14 discussed herein. The basket sieve includes a sieve surface 54*c* and a lip 56*c*. The sieve surface 54*c* is configured to pass the D-cells 64 from a biopsy but not solid tissue 62 from the biopsy. The lip 56*c* is configured to rest on a corresponding ledge or ridge line of the sample collection container 16*c*. As illustrated, the lip 56*c* can be wider on one side of the basket sieve 14*c* than another. As seen in FIG. 14, the basket sieve 14*c* is sized and shaped to be sealed within a corresponding specimen cup 66 with the solid tissue 16 and sent to a tissue pathology lab.

Figure 15:
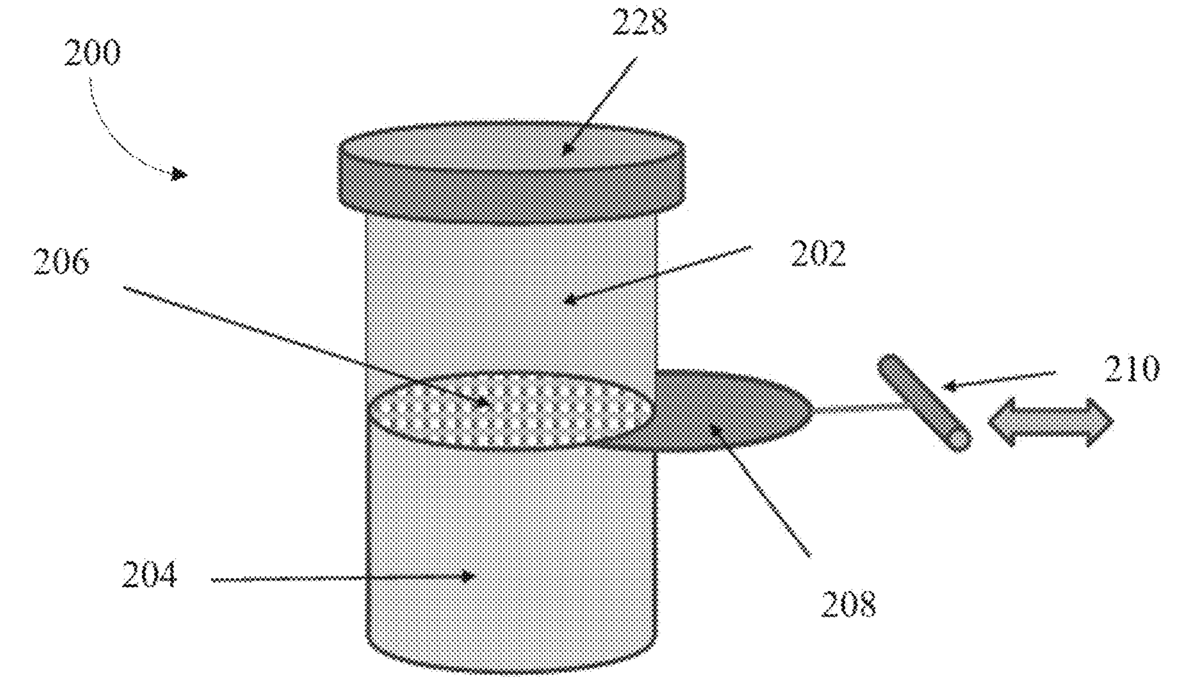
FIGS. 15 and 16 illustrate a fifth example embodiment of a biopsy container apparatus in accordance with the present disclosure.
Figure 16:
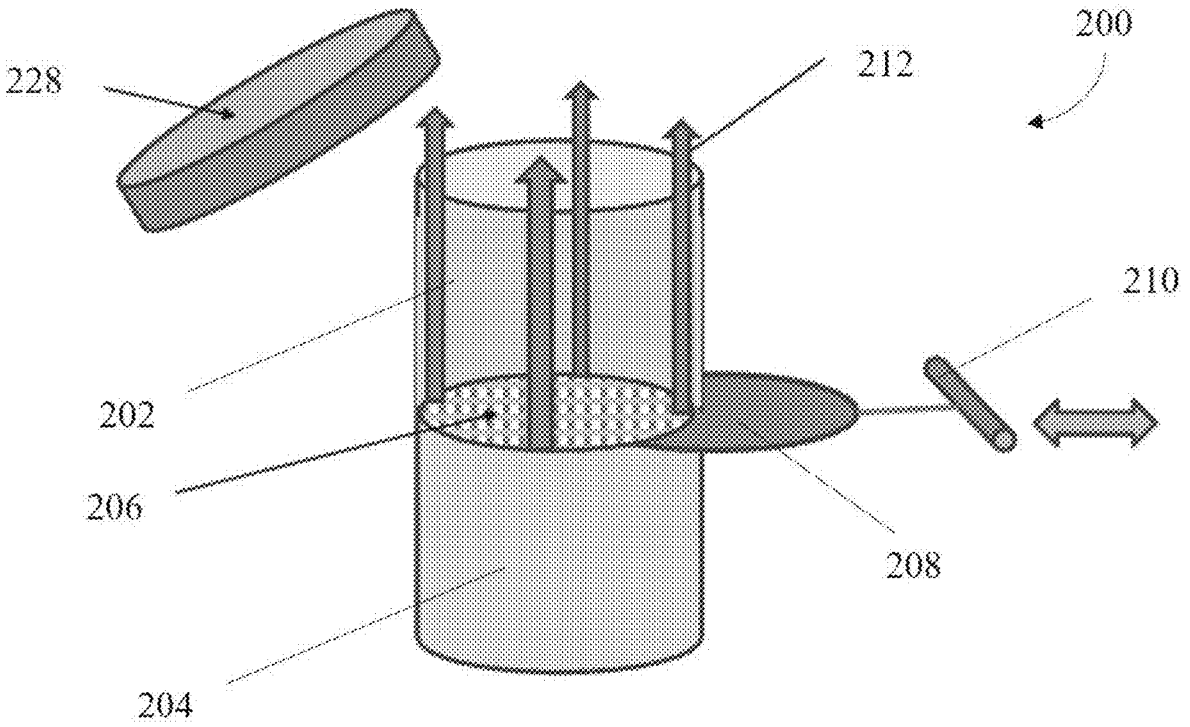

FIGS. 14 and 15 illustrate an alternative example embodiment of a biopsy container apparatus 200. Those of ordinary skill in the art will recognize that various elements of the biopsy container apparatus 200 can be modified with various elements of the other embodiments of biopsy containers discussed herein, and vice versa.

In the illustrated embodiment, the biopsy container apparatus 200 includes an upper chamber 202 and a lower chamber 204 which are separated by a sieve surface 206 and a solid surface 208. The sieve surface 206 is located between the upper chamber 202 and the lower chamber 204 and is configured to pass the dislodged cells 64 from a biopsy but not the solid tissue 62 from the biopsy. The solid surface 208 is movably attached with respect to the sieve surface 206 and configured to translate between (i) a first configuration in which the solid surface 208 overlaps the sieve surface 206 to prevent the D-cells 64 from passing through the sieve surface 206 and (ii) a second configuration in which the solid surface 208 is moved away from the sieve surface 206 to permit the D-cells 64 to pass though the sieve surface 206 from the upper chamber 202 to the lower chamber 204.

In the illustrated embodiment, the biopsy container apparatus 200 includes a handle 210 attached to the solid surface 208. The handle 210 enables a user to translate the solid surface 208 in a perpendicular direction with respect to the height of the biopsy container apparatus 200 as shown in FIGS. 14 and 15. More specifically, the handle 210 enables a user to pull the solid floor 208 out from between the upper chamber 202 and the lower chamber 204 and away from the sieve surface 206, and then to push the solid floor 208 back in between the upper chamber 202 and the lower chamber 204 so that it overlaps with the sieve surface 206 in the vertical direction of FIGS. 14 and 15. When the solid floor 208 is pulled to the side, the sieve surface 206 allows the dislodged cells 64 to pass into the lower chamber 204, but retains the solid tissue 62 in the upper chamber 202. As illustrated, the biopsy container apparatus 200 also includes a lid 208 that attaches to the upper chamber 202.

In use, a radiologist user who takes a needle biopsy unscrews the lid 228 from the upper chamber 202, places the core needle 60 including solid tissue 62 and D-cells 64 into upper chamber 202, and swirls the core needle 60 to dislodge the solid tissue 62 and D-cells 64. The user then pulls the handle 210 to pull the solid surface 208 from between the upper chamber 202 and the lower chamber 204 and away from the sieve surface 206, releasing the D-cells 64 into buffer solution into the lower chamber 204, where they mix with a reagent (e.g. Zymo DNA/RNA Shield™ reagent) in the lower chamber 204. The user then pushes handle 210 back to its original position, sealing the D-cells 64 in solution in the lower chamber 204, then tilts the biopsy container apparatus 200 upside down to release the solid tissue 62 from the upper chamber 202 into a standard formalin-containing vial for transport to paraffin preparation lab. The user the screws the lid 228 back on, and sends the biopsy container apparatus 200 containing the D-cells 64 in solution for molecular testing. As seen in FIG. 15, the biopsy container apparatus 200 can also include vertical projections 212 that enable the sieve surface 206 holding the solid tissue 62 to be removed from the biopsy container apparatus 200 and placed into the standard formalin-containing vial for transport to paraffin preparation lab.

The embodiments described herein provide improved apparatuses and methods for segregating tissue samples for multiple diagnostic modalities. An advantage of the disclosed apparatuses and methods is that D-cells can be collected at the site of the procedure, in an easy to perform process that almost completely eliminates pre-analytic variation and more importantly, before exposure to formalin fixation. This front-end approach, where the collection and stabilization occurs before fixation, is in contrast to other proposed biopsy substrate shortage solutions that seek to improve the substrate after it has already been fixed in formalin and damaged (back-end approaches). Prototype testing has shown that the specimen collected as D-cells by using this method result in more than sufficient amounts of nucleic acids, that are also of high quality, for molecular studies.

It should be understood that various changes and modifications to the apparatuses and methods described herein will be apparent to those skilled in the art and can be made without diminishing the intended advantages.

General Interpretation of Terms

In understanding the scope of the present invention, the term "comprising" and its derivatives, as used herein, are intended to be open-ended terms that specify the presence of the stated features, elements, components, groups, and/or steps, but do not exclude the presence of other unstated features, elements, components, groups, integers and/or steps. The foregoing also applies to words having similar meanings such as the terms, "including". "having" and their derivatives. Also, the terms "part," "section," or "element" when used in the singular can have the dual meaning of a single part or a plurality of parts.

The term "configured" as used herein to describe a component, section or part of a device includes hardware that is constructed to carry out the desired function.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such features. Thus, the foregoing descriptions of the embodiments according to the present invention are provided for illustration only, and not for the purpose of limiting the invention as defined by the appended claims and their equivalents.

What is claimed is:

1. A biopsy container apparatus for recovering solid tissue and dislodged cells ("D-cells") from a biopsy, the biopsy container apparatus comprising:

a sample collection container including a reagent chamber;

a basket sieve configured for removable attachment at least partially within the sample collection container, the basket sieve including a sieve surface configured to pass the D-cells from the biopsy but not the solid tissue from the biopsy; and a buffer container configured for removable attachment to the sample collection container, the buffer container including a buffer chamber with a bottom that is sealed and watertight.

2. The biopsy container apparatus of claim 1, wherein the buffer container includes a funnel portion configured to guide the solid tissue and the D-cells from the biopsy into the buffer chamber.

3. The biopsy container apparatus of claim 2, wherein the buffer container is configured for attachment to the sample collection container with the buffer chamber at least partly located within the sample collection container, and with the funnel portion at least partly located outside of the sample collection container.

4. The biopsy container apparatus of claim 1, wherein the sample collection container includes a ledge or ridge line configured to suspend the basket sieve within the sample collection container above the reagent chamber.

5. The biopsy container apparatus of claim 1, wherein
the buffer container includes a first attachment mechanism,
the sample collection container includes a second attachment mechanism, and
the buffer container is removably attached to the sample collection container by cooperation between the first attachment mechanism and the second attachment mechanism.

6. The biopsy container apparatus of claim 5, wherein the first attachment mechanism and the second attachment mechanism include corresponding threads enabling the buffer container to be screwed into the sample collection container.

7. The biopsy container apparatus of claim 5, wherein the first attachment mechanism and the second attachment mechanism include rubber sleeves enabling the buffer container to removably attach to the sample collection container.

8. The biopsy container apparatus of claim 1, comprising a lid that fits both the sample collection container and the buffer container.

9. The biopsy container apparatus of claim 1, wherein
the sample collection container is pre-filled with a reagent in the reagent chamber, and
the buffer container is pre-filled with a buffer solution in the buffer chamber.

10. The biopsy container apparatus of claim 9, wherein
the sample collection container includes between 1 and 2 mL of reagent, and
the buffer container includes between 1 and 2 mL of buffer solution.

11. The biopsy container apparatus of claim 9, wherein
the sample collection container includes a first amount of reagent, and
the buffer container includes a second amount of buffer solution that is approximately equal in volume to the first amount of reagent.

12. The biopsy container apparatus of claim 1, wherein the buffer container includes a skirt configured to removably attach the sample collection container.

13. The biopsy container apparatus of claim 9, wherein the buffer solution includes a saline solution.

14. A method of recovering solid tissue and dislodged cells ("D-cells") from a biopsy using a biopsy container apparatus including a buffer container, a basket sieve and a sample collection container, the method comprising:
depositing the solid tissue and the D-cells from the biopsy into a buffer chamber of the buffer container with a bottom that is sealed and watertight to retain a buffer solution within the buffer container;
removing the buffer container from the basket sieve and the sample collection container;
pouring the solid tissue, the D-cells and the buffer solution into the basket sieve while the basket sieve is located within the sample collection container;
removing the basket sieve with the solid tissue from the sample collection container;
placing the basket sieve with the solid tissue into a sealed container for tissue processing; and
sealing a mixture including the D-cells, the buffer solution and the reagent for diagnostic testing.

15. The method of claim 14, comprising
depositing the solid tissue and the D-cells from a core needle into the buffer chamber.

16. The method of claim 14, wherein
sealing the mixture including the D-cells, the buffer solution and the reagent includes sealing the mixture within the sample collection container.

17. The method of claim 14, comprising
receiving the biopsy container apparatus with the buffer container, the basket sieve and the sample collection container attached together.

18. The method of claim 17, comprising
receiving the biopsy container apparatus with the sample collection container pre-filled with a reagent, the basket sieve located at least partially within the sample collection container, and the buffer container pre-filled with the buffer solution and located at least partially within the sample collection container.

19. The method of claim 14, comprising
removing a lid from the buffer container before depositing the solid tissue and the D-cells from the biopsy into the buffer container, and
wherein sealing the mixture including the D-cells, the buffer solution and the reagent for diagnostic testing includes sealing the D-cells, the buffer solution and the reagent within the sample collection container using the lid.

* * * * *